United States Patent
Tammer et al.

(10) Patent No.: US 11,407,714 B2
(45) Date of Patent: Aug. 9, 2022

(54) PROCESS FOR PRODUCING AN ORGANIC PEROXIDE

(71) Applicant: NOURYON CHEMICALS INTERNATIONAL B.V., Arnhem (NL)

(72) Inventors: Martinus Catharinus Tammer, Diepenveen (NL); John Hendrik Jacob Van Der Linden, Bad Bentheim (DE); Pattama Saisaha, Breda (NL); Maria Steensma, Arnhem (NL)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 17/310,738

(22) PCT Filed: Jan. 31, 2020

(86) PCT No.: PCT/EP2020/052464
§ 371 (c)(1),
(2) Date: Aug. 20, 2021

(87) PCT Pub. No.: WO2020/169322
PCT Pub. Date: Aug. 27, 2020

(65) Prior Publication Data
US 2022/0106269 A1    Apr. 7, 2022

(30) Foreign Application Priority Data

Feb. 22, 2019  (EP) ..................................... 19158837

(51) Int. Cl.
*C07C 407/00*     (2006.01)

(52) U.S. Cl.
CPC ............................... *C07C 407/003* (2013.01)

(58) Field of Classification Search
CPC ......................... C07C 407/00; C07C 407/003
See application file for complete search history.

(56) References Cited

U.S. PATENT DOCUMENTS 4,168,274 A    9/1979  Hildon et al.

FOREIGN PATENT DOCUMENTS

| CN | 101857563 A | 10/2010 |
| CN | 108658824 A | 10/2018 |
| GB | 1501356 A | 2/1978 |

*Primary Examiner* — Sikarl A Witherspoon
(74) *Attorney, Agent, or Firm* — Lorenz & Kopf, LLP

(57) ABSTRACT

This present disclosure relates to a process for producing an organic peroxide and isolating, purifying, and concentrating the sulfuric acid from the aqueous effluents of said organic peroxide production process.

19 Claims, No Drawings

and is not intended to limit the present disclosure or

PROCESS FOR PRODUCING AN ORGANIC PEROXIDE

CROSS-REFERENCE TO RELATED APPLICATION

This application is a U.S. National-Stage entry under 35 U.S.C. § 371 based on International Application No. PCT/EP2020/052464, filed Jan. 31, 2020 which was published under PCT Article 21(2) and which claims priority to European Application No. 19158837.5, filed Feb. 22, 2019, which are all hereby incorporated in their entirety by reference.

TECHNICAL FIELD

The present disclosure relates to an acid catalysed process for producing an organic peroxide. Several organic peroxide production processes are acid catalysed and require the use of large amounts of strong acid. The preferred acid to be used is sulfuric acid. The use of large amounts of sulfuric acid leads to the formation of large amounts of sulfate-containing waste streams.

BACKGROUND

Recycling of streams in a process to produce organic peroxides from alcohols or ketones is known from CN 101857563 and CN 108658824. CN101857563 and CN 108658824 disclose a process to prepare tertbutyl hydroperoxide by reacting tert butanol and hydrogen peroxide in the presence of sulfuric acid in which part of the mother liquor is recycled to be reused as solvent for newly added reactants. To avoid an indefinite dilution of the process streams the mother liquor is only recycled partly. Because only part of the mother liquor is recycled into the process only part of the sulfuric acid and unreacted hydrogen peroxide and tert butanol are reused. Effectively, the majority of the sulfuric acid employed will end up as a waste stream in the process as disclosed.

BRIEF SUMMARY

This disclosure provides a process for producing an organic peroxide, said process comprising the following steps:
a. reacting an alcohol or ketone with hydrogen peroxide, thereby forming a reaction mixture comprising:
   an organic phase comprising an organic peroxide; and
   an aqueous phase comprising (i) at least about 5 wt % $H_2SO_4$ and (ii) $H_2O_2$ and/or organic peroxide residues,
b. separating the aqueous phase from the organic phase,
c. optionally adding $H_2O_2$ to, and/or removing any residual organic compounds from, the aqueous phase,
d. obtaining an additional aqueous phase comprising from about 5-about 60 wt % $H_2SO_4$ and about 0.3-about 35 wt % $H_2O_2$, and
e. heating the additional aqueous phase of step d. at a temperature of from about 20-about 300° C., at a pressure of about 0.001 to about 1 bar, thereby decomposing at least part of the $H_2O_2$, removing part of the water, and increasing the $H_2SO_4$ concentration of the additional aqueous phase by at least about 7 weight percentage points to a concentration of from about 12-about 95 wt %.

DETAILED DESCRIPTION

The following detailed description is merely exemplary in nature and is not intended to limit the present disclosure or the application and uses of the present disclosure. Furthermore, there is no intention to be bound by any theory presented in the preceding background of the present disclosure or the following detailed description.

The organic peroxide production process according to the present disclosure comprises the following steps:
a. reacting an alcohol or ketone with hydrogen peroxide, thereby forming a reaction mixture comprising:
   an organic phase comprising an organic peroxide and
   an aqueous phase comprising (i) at least about 5 wt % $H_2SO_4$ and (ii) $H_2O_2$ and/or organic peroxide residues,
b. separating the aqueous phase from the organic phase,
c. optionally adding $H_2O_2$ to and/or removing any residual organic compounds from said aqueous phase,
d. obtaining an aqueous phase comprising about 5-about 60 wt % $H_2SO_4$ and about 0.3-about 35 wt % $H_2O_2$, and
e. heating the aqueous phase of step d. at a temperature in the range from about 20-about 300° C., at a pressure of about 0.001 to about 1 bar, thereby decomposing at least part of the $H_2O_2$, removing part of the water, and increasing the $H_2SO_4$ concentration of the aqueous mixture by at least about 7 weight percentage points to a concentration in the range from about 12-about 95 wt %.

This object to further reduce sulfate-containing waste streams has been met by the process of the present disclosure, which includes steps for the purification, concentration, and re-use of the sulfuric acid stream originating from an organic peroxide production process.

The sulfuric acid stream contains peroxide: hydrogen peroxide, residues of the organic peroxide that was produced, or a combination thereof. It will also contain other organic species. In order to be re-used, it is essential that the sulfuric acid is purified from organic residues. It is also essential to concentrate the sulfuric acid to a concentration that is required for its re-use. Furthermore, peroxide residues have to be removed from the stream, because not all process steps in which the purified and recycled stream will be used allow the presence of peroxide residues.

Quite unexpectedly, the sulfuric acid containing stream can be concentrated by a simple step, above step e), in which water is evaporated. As known by those skilled in the art, when reacting an alcohol or ketone with a hydrogen peroxide in the presence of sulfuric acid, the formation of acetone peroxides cannot be prevented. Acetone peroxides bear the risk of solidifying in a water evaporation step such as above step e), and acetone peroxide crystals are known to be friction sensitive explosives. However, in the process of the present disclosure the acetone peroxide buildup and formation of colored products is unexpectedly suppressed by the combination of steps c), d) and e) of the process of the present disclosure and the amount of acetone peroxide remains below the level at which it can create safety problems It should be noted that U.S. Pat. No. 4,168,274 and GB1501356 disclose a process that involves the recycling of a sulfuric acid waste stream in which a concentration step of the sulfuric acid solution is present. However, these documents relate to the preparation of a peracid by reacting an organic acid with hydrogen peroxide in the presence of sulfuric acid. When preparing peracids by reacting acids with hydrogen peroxide, contrary to when reacting alcohols or ketones with hydrogen peroxide, as a person skilled in the art is aware, acetone peroxides will not be formed.

The aqueous phase resulting from step e. can be used for any purpose for which it is suitable, such as the production of phosphoric acid from phosphate rock, the production of ammonium sulfate from coking plants, the production of aluminium sulfate from bauxite, the manufacture of dyestuff solutions, the production of hydrogen via the sulfur-iodine cycle (Bunsen reaction), as industrial cleaning solution, or as electrolyte in e.g. lead-acid batteries.

In a preferred embodiment, at least part of the aqueous phase resulting from step e. is re-used in an organic peroxide production process. This can be the same process, for the same organic peroxide, as it resulted from, but may also be a process for the production of another organic peroxide.

The advantage of the present process is that it does not require the addition of contaminating materials, such as metals, which makes the recycled sulfuric acid suitable for re-use in a peroxide production process.

In a more preferred embodiment, at least part of the aqueous phase resulting from step e. is re-cycled to step a.

The aqueous phase that is treated in steps c., d., and e. can result from one specific organic peroxide production process, but may also be a mixture of the aqueous phases resulting from two or more different organic peroxide production processes.

Increasing the H2SO4 concentration in step e. by heating the aqueous phase is not so straightforward as it may seem. The H2O2 that is present in said phase will decompose, which can result in significant oxygen gas formation and, consequently, pressure build-up. Furthermore, this oxygen, together with volatile organics, can form a flammable and potentially explosive mixture.

The alcohol that is employed in step a) in embodiments is chosen from the group consisting of tert-butyl alcohol, tert-amyl alcohol, 1,1,3,3-tetramethylbutanol, 2,5-dimethyl-2,5-hexanediol, 2-methyl-2,4-pentanediol, 2,5-dimethyl-2,5-dihydroxy-hexyne-3, 1,3-bis(isopropanol)benzene, and 1,4-bis(isopropanol)benzene The ketone that is employed in step a) in embodiments is chosen from group consisting of acetone, acetyl acetone, methyl ethyl ketone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, ethyl amyl ketone, methyl octyl ketone, methyl nonyl ketone, cyclopentanone, cyclohexanone, 2-methylcyclohexanone, 3,3,5-trimethyl cyclohexanone The reaction of step a) is done in the presence of H2SO4.

Suitable organic peroxides that can be produced according to the process of the present disclosure are dialkyl peroxides, cyclic ketone peroxides, trioxepanes, and aliphatic hydroperoxides.

Specific examples of dialkyl peroxides are 2,2-di(tert-butylperoxy)butane, dicumyl peroxide, di(tert-butylperoxy-isopropyl)benzene, 2,5-dimethyl-2,5-di(tert-butylperoxy) hexane, di-tert-butylperoxide, di-tert-amylperoxide, 2,5-dimethyl-2,5-di(tert-butylperoxy)hexyne-3, and tert-butyl cumyl peroxide.

Preferred dialkyl peroxides are 2,5-dimethyl-2,5-di(tert-butylperoxy)hexane, 2,5-dimethyl-2,5-di(tert-butylperoxy) hexyne-3, di-tert-amylperoxide, and di-tert-butylperoxide. The production of these peroxides requires relatively concentrated sulfuric acid solutions (about 30 wt % or higher).

The term "cyclic ketone peroxides" includes dimeric cyclic ketone peroxides and trimeric cyclic ketone peroxides. These peroxides have the following structures:

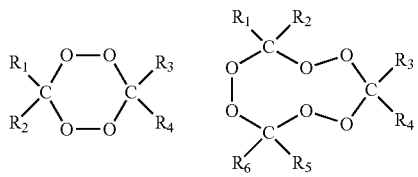

wherein R1-R6 are independently selected from the group consisting of hydrogen, C1-C20 alkyl, C3-C20 cycloalkyl, C6-C20 aryl, C7-C20 aralkyl, and C7-C20 alkaryl, which groups may include linear or branched alkyl moieties; and each of R1-R6 may optionally be substituted with one or more groups selected from hydroxy, alkoxy, linear or branched alkyl, aryloxy, ester, carboxy, nitrile, and amido.

Preferred cyclic ketone peroxides are 3,6,9-triethyl-3,6, 9-trimethyl-1,4,7-triperoxonane (3MEK-cp) and mixtures comprising 3MEK-cp and at least one peroxide satisfying formula

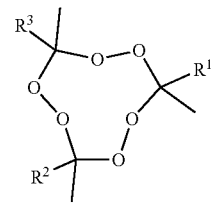

wherein R1 through R3 are independently selected from alkyl and alkoxyalkyl groups, said groups having about 2 to about 5 carbon atoms, the total number of carbon plus oxygen atoms of R1+R2+R3 is in the range from about 7-about 15. The term alkoxyalkyl group refers to a group with the formula —CnH2n-O—CmH2m+1, wherein both n and m are at least about 1.

Trioxepanes have the formula

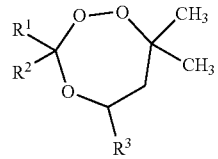

wherein R1, R2, and R3 are independently selected from hydrogen and a substituted or unsubstituted hydrocarbyl group, and optionally two of the group of R1, R2, and R3 are linked to form a ring structure. Preferably, R1, R2, and R3 are independently selected from the group consisting of hydrogen and substituted or unsubstituted C1-C20 alkyl, C3-C20 cycloalkyl, C6-C20 aryl, C7-C20 aralkyl, and C7-C20 alkaryl, which groups may include linear or branched alkyl moieties, while two of R1, R2, and R3 may be connected to form a (substituted) cycloalkyl ring; the optional one or more substituents on each of R1-R3 being selected from the group consisting of hydroxy, alkoxy, linear or branched alk(en)yl, aryloxy, halogen, carboxylic acid, ester, carboxy, nitrile, and amido.

Preferably, R1 and R3 are selected from lower alkyl groups, more preferably C1-C6 alkyl groups, such as methyl, ethyl, and isopropyl, methyl and ethyl being most preferred. R2 is preferably selected from hydrogen, methyl, ethyl, iso-propyl, iso-butyl, tert-butyl, amyl, iso-amyl, cyclohexyl, phenyl, CH3C(O)CH2-, C2H5OC(O)CH2-, HOC(CH3)2CH2-, and

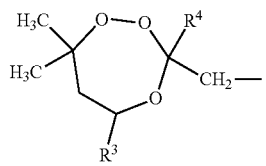

wherein R4 is independently selected from any of the group of compounds given for R1-3. Another preferred trioxepane is:

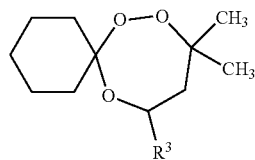

Specific examples of aliphatic hydroperoxides are tert-butyl hydroperoxide, tert-amyl hydroperoxide, hexyleneglycol hydroperoxide, 2,5-dimethyl-2,5-dihydroperoxy hexane, 2,5-dimethyl-2,5-dihydroperoxy-3-hexyne, and 1,1,3,3-tetramethylbutyl hydroperoxide, and 1,1-dimethylbutyl hydroperoxide.

If a mono-alcohol is used in step a. of the process, a dialkyl peroxide or a hydroperoxide results, depending on the amount of hydrogen peroxide and the sulfuric acid concentration. For dialkylperoxide production, an aqueous sulfuric acid solution with a concentration of at least about 30 wt % is generally required; for hydroperoxides, a concentration between about 10 and about 30 wt % is generally used.

Examples of suitable mono-alcohols are tert-butyl alcohol, tert-amyl alcohol, and 1,1,3,3-tetramethylbutanol.

If a di-alcohol is used in step a. of the process, a di-hydroperoxide results, which can be further reacted with a mono-alcohol, also in the presence of sulfuric acid, towards a bis-dialkyl peroxide. Aqueous sulfuric acid solutions with a concentration of at least 10 wt % are preferably used in the latter reaction.

Examples of di-alcohols are 2,5-dimethyl-2,5-hexanediol, 2,5-dimethyl-2,5-dihydroxy-hexyne-3, 1,3-bis(isopropanol)benzene, and 1,4-bis(isopropanol)benzene.

In order to obtain a dimeric or trimeric cyclic ketone peroxide, a ketone is reacted with hydrogen peroxide in the presence of a 20-75 wt % aqueous sulfuric acid solution and an inert diluent (phlegmatizer). Examples of suitable ketones are linear, branched or cyclic C3-C13 ketones, most preferably C3-C7 ketones. Examples of suitable ketones are acetone, acetyl acetone, methyl ethyl ketone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, ethyl amyl ketone, methyl octyl ketone, methyl nonyl ketone, cyclopentanone, cyclohexanone, 2-methylcyclohexanone, 3,3,5-trimethyl cyclohexanone, and mixtures thereof.

Trioxepanes are obtained by reacting a glycol (dialcohol) with hydrogen peroxide in the presence of from about 20-about 60 wt % aqueous sulfuric acid solution, in order to form a glycol hydroperoxide. The glycol hydroperoxide is subsequently reacted with a ketone or aldehyde, again in the presence sulfuric acid (from about 10-about 60 wt % aqueous solution), to form the trioxepan. This process is described in WO 2006/066984.

A suitable example of a glycol is 2-methyl-2,4-pentanediol.

The formed organic peroxide will be present in the organic layer of the resulting bi-phasic reaction mixture and can be isolated by conventional techniques, such as gravity, a liquid/liquid separator, a centrifuge, or a continuous (plate) separator (step b.).

The organic peroxide is generally washed with water or an alkaline aqueous solution.

The aqueous phase will contain (i) H2SO4 and (ii) H2O2 and/or remaining organic peroxide. It may also contain additional organics. These organics in preferred embodiments need to be substantially removed and/or destroyed, in order to prevent them from blackening the aqueous mixture or to build up to an undesired level.

In preferred embodiments these organics are more completely removed and/or destroyed by (vacuum) distillation (step e.) or by adding an (additional) amount of hydrogen peroxide to the aqueous mixture (step c.).

The aqueous phase of step d. preferably contains at least about 5 wt %, preferably at least about 10 wt %, more preferably at least about 20 wt %, and most preferably at least about 30 wt % H2SO4. It preferably contains not more than about 60 wt % H2SO4.

In addition to H2SO4, other acids may be present in the aqueous phase.

The aqueous phase of step d. comprises from about 0.3-35 wt %, preferably about 0.5-about 35 wt %, more preferably about 1-about 35 wt %, even more preferably about 2-about 35 wt %, and most preferably about 2-about 25 wt % H2O2.

In order to decompose at least part of the H2O2, remove part of the water, and raise the H2SO4 concentration by at least about 7 weight percentage points to a concentration in the range from about 12-about 95 wt %, preferably about 50-about 95 wt %, more preferably about 70-about 95 wt %, and most preferably about 75-about 85 wt %, the aqueous mixture is heated to a temperature in the range from about 20-about 300° C., preferably about 30-about 250° C., even more preferably about 50-about 200° C., and most preferably about 100-about 200° C., at a pressure of from about 0.001-about 1 bar, preferably about 0.01-about 1 bar (step e.).

It should be noted that the temperature of the aqueous phase formed in step b. is generally in the range from about 0-about 20° C., preferably about 0-about 10° C., as peroxide production processes are often performed at low temperatures.

It is not desired to concentrate to ≥ about 96 wt % H2SO4, as that requires distillation of SO3 and its subsequent dissolution.

The heating is preferably conducted in one or more distillation and/or heating steps.

The heating step in a preferred embodiment involves stripping of volatile organic components at temperatures below the decomposition temperature of H2O2. Suitable temperatures are in the range from about 30-about 120° C. The pressure can be atmospheric but is preferably lower, in order to avoid an explosive atmosphere during the process.

If the hydrogen peroxide concentration of the aqueous mixture is relatively high (about 2 wt % or more), its decomposition will result in a substantial oxygen stream. Distillation at atmospheric pressure is then preferred in view of safety concerns.

If the peroxide concentration is lower, or gets lower during the process, distillation at reduced pressure should be considered. It is also possible to first apply atmospheric distillation, followed by distillation at reduced pressure.

The aqueous distillate that is removed during step e. is condensed in a condenser and subsequently collected in a vessel.

Due to the decomposition of hydrogen peroxide, the distillate will contain significant amounts of oxygen. The oxygen will not condense in the condenser and in order to ensure safe processing it is required to keep the oxygen concentration of the distillate below the flashpoint. Preferably, the oxygen concentration in the gas phase is kept below about 30 vol %, preferably below about 8 vol %.

This can be achieved by introducing nitrogen or air into the system, thereby diluting the oxygen. More preferably, a nitrogen or air stream is added to the distillate before entering the condenser, or while present in the condenser.

Step e. can be conducted batch-wise, semi-continuously or continuously. In a batch process with higher volumes, the temperature should be carefully controlled to prevent dangerous situations. Furthermore, in batch processes most gas is formed at the beginning of the process, which may lead to the establishment of very concentrated oxygen streams. With concentrated oxygen streams, it is difficult to control the nitrogen stream such that the mixture stays below the flashpoint. In (semi)continuous operation, however, the rate of oxygen and CO2 formation will be more to almost completely constant and the oxygen concentration will be much easier to control. In semi-continuous mode, a first portion of the aqueous phase is heated to boiling temperature in a batch reactor; then the remaining portion of the aqueous phase containing H2SO4 and H2O2 is dosed to said batch reactor and (part of) the concentrated acid is taken out intermittently. In this way, the rate of oxygen formation and organics stripping is also more efficient and better controllable. Continuous operation or semi-continuous operation is preferred.

In a specific embodiment, the process relates to the production of 2,5-di-tert-butylperoxy-2,5-dimethylhexane or 2,5-di-tert-butylperoxy-2,5-di(tert-butylperoxy)hexyne-3. These peroxides are conventionally prepared in two steps. In the first step, 2,5-dimethyl-2,5-hexanediol, resp. 2,5-dimethyl-2,5-dihydroxy-hexyne-3, is reacted with hydrogen peroxide, in the presence of sulfuric acid, towards 2,5-dihydroperoxy-2,5-dimethylhexane, resp. 2,5-dihydroperoxy-2,5-dimethylhexyne-3. An excess of hydrogen peroxide in a high concentration (e.g. an about 70 wt % aqueous solution) is generally required, including a relatively large amount of highly concentrated sulfuric acid (e.g. an about 70-about 95 wt % aqueous solution). The dihydroperoxide can be isolated from the aqueous effluent by filtration or centrifugation and contains significant amounts of sulfuric acid, hydrogen peroxide, a little diol, and various organic byproducts.

The dihydroperoxide is then reacted with tert-butanol, again catalyzed by highly concentrated sulfuric acid (e.g. am about 60-about 90 wt % aqueous solution), to form the desired peroxide. The aqueous effluent from this step, which may also be obtained by gravity separation or centrifugation, will contain sulfuric acid and organic byproducts.

The combined aqueous effluents comprise about 10-about 50 wt % H2SO4 and about 5-about 20 wt % H2O2. Organics can be removed from the resulting aqueous phase by stripping with an air stream, followed by a distillation to destroy most of the H2O2, and increase the H2SO4 concentration. A further distillation at reduced pressure may be performed thereafter to further increase the H2SO4 concentration.

The resulting purified and concentrated H2SO4 can be used in various processes. In a preferred embodiment, it is re-used in the first and/or second step of this peroxide production process.

In another specific embodiment, the process relates to the production of di-tert-butyl peroxide or di-tert-amyl peroxide. According to this embodiment, tert-butyl alcohol or tert-amyl alcohol is reacted with hydrogen peroxide in the presence of a about 30-about 78 wt % aqueous sulfuric acid solution, to form di-tert-butyl peroxide or di-tert-amyl peroxide, respectively.

The organic and aqueous phases can be separated by gravity, centrifugation, a liquid/liquid separator, or a continuous (plate) separator.

The aqueous phase contains from about 5-about 70 wt % H2SO4, about 0.1-about 10 wt % tert-butanol or tert-amyl alcohol, and about 0.1-about 5 wt % organic peroxide.

Hydrogen peroxide is then dosed to the aqueous phase, resulting in an aqueous phase with a hydrogen peroxide concentration of from about 0.3-about 20 wt %, preferably about 0.3-about 10 wt %, and most preferably about 0.3-about 5 wt %. This mixture is then preferably stirred at a temperature in the range from about 50-about 250° C., more preferably about 80-about 220° C., most preferably about 100-about 210° C., optionally under reduced pressure, in order to destroy and/or remove organic residues and increase the sulfuric acid concentration.

In another embodiment, the process relates to the production of hydroperoxides. According to this embodiment, a tertiary alcohol or a substituted alkene is reacted with hydrogen peroxide in the presence of sulfuric acid (about 5-about 95 wt % aqueous solution) to form tert-alkyl hydroperoxides.

The organic and aqueous phases can be separated by gravity, centrifugation, a liquid/liquid separator, or a continuous (plate) separator.

The aqueous phase contains from about 5-about 60 wt % H2SO4, about 1-about 25 wt % H2O2, about 0.1-about 20 wt % tertiary alcohol, and about 0.1-about 5 wt % organic peroxides.

Hydrogen peroxide is then optionally dosed to the aqueous phase, which is then preferably stirred at a temperature in the range from about 50-about 250° C., more preferably about 80-about 220° C., most preferably about 100-about 210° C., optionally under reduced pressure, in order to destroy and/or remove organic residues and increase the sulfuric acid concentration.

In another embodiment, the process relates to the production of trimeric cyclic ketone peroxides.

According to this embodiment, a ketone is reacted with hydrogen peroxide in the presence of from about 20-about 95 wt % aqueous sulfuric acid solution, to form trimeric cyclic ketone peroxides.

The organic and aqueous phases can be separated by gravity, centrifugation, a liquid/liquid separator, or a continuous (plate) separator.

The aqueous phase contains from about 20-about 70 wt % H2SO4, about 1-about 25% H2O2, about 0.1-about 20 wt % ketones, and about 0.1-about 10 wt % organic peroxides.

Hydrogen peroxide optionally is then dosed to the aqueous phase, which is then preferably stirred at a temperature in the range from about 50-about 250° C., more preferably about 80-about 220° C., most preferably about 100-about 210° C., optionally under reduced pressure, in order to destroy and/or remove organic residues and increase the sulfuric acid concentration.

In another embodiment, the process relates to the production of trioxepanes.

According to this embodiment, a ketone is reacted with a hydroxyl hydroperoxide in the presence of from about 20-about 95 wt % aqueous sulfuric acid solution, to form trioxepanes.

The organic and aqueous phases can be separated by gravity, centrifugation, a liquid/liquid separator, or a continuous (plate) separator.

The aqueous phase contains from about 10-about 70% wt % $H_2SO_4$, about 0.1-about 20 wt % ketones, and about 0.1-about 20 wt % organic peroxides Hydrogen peroxide is then optionally dosed to the aqueous phase, which is then preferably stirred at a temperature in the range from about 50-about 250° C., more preferably about 80-about 220° C., most preferably about 100-about 210° C., optionally under reduced pressure, in order to destroy and/or remove organic residues and increase the sulfuric acid concentration.

EXAMPLES

Example 1

An aqueous 70 wt % hydrogen peroxide solution (121.6 g) was added to a jacketed reactor. The reactor was cooled to 5° C. An aqueous 78 wt % sulfuric acid solution (157.5 g) was then dosed to the reactor within 20 minutes, while the temperature of the mixture was controlled below 10° C. After addition of the sulfuric acid, the mixture was cooled to 5° C. Solid 2,5-dimethyl-2,5-dihydroxy hexane (36.6 grams, 0.25 moles) was added to the mixture at such a rate that the temperature stayed below 10° C.

After the addition of the 2,5-dimethyl-2,5-dihydroxy hexane, the temperature was raised to 25° C. and kept at this temperature for one hour. The temperature was subsequently reduced to 5° C. and 200 mL water was added. After 2 minutes of agitation, the reaction mixture was filtered and washed with cold water. Solid 2,5-dimethyl-2,5-dihydroperoxyhexane was obtained in a yield of 78%. The 471 g aqueous phase containing 26% $H_2SO_4$ was combined with the acid layer of the next step.

Tert-butanol (88 wt % in water, 143 grams, 1.7 moles) was added (20 min) dropwise into a stirred solution of sulfuric acid (78 wt %, 104.7 grams, 0.83 moles) in a jacketed reactor held at 15° C. 2,5-Dimethylhexane-2,5-dihydroperoxide obtained in the previous step (54 g, 0.20 moles) was added in 20 min., after which the temperature was raised to 40° C. and kept at this temperature for up to four hours.

The reaction resulted in a two-layer mixture; the layers of which were separated by draining off the aqueous layer. The organic layer contained 2,5-dimethyl-2,5-di-tert-butylperoxyhexane in a yield of 70%.

The aqueous layer was diluted with 150 g water and tert-butanol was removed by distillation at 100 mbar. The resulting 276 g aqueous phase containing 30 wt % $H_2SO_4$ was combined with the aqueous phase of the first step, thereby forming a waterphase containing 27 wt % $H_2SO_4$ and 9 wt % $H_2O_2$.

Said waterphase was dosed just below the top of a glass vigreux column that was mounted on a three necked glass vessel. The vessel was stirred and the temperature was maintained at from about 135-140° C. by heating with an external oil bath at atmospheric pressure. The vigreux column was connected to a condenser (at 20° C.) and a vessel to collect the condensate. Air was fed to the condenser in order to dilute the oxygen content in the gas phase to 25 vol %. The waterphase was dosed to the vigreux column at a rate of 5 gram per minute, resulting in the formation of a condensate at a rate of 2.65 gram per minute. No solids (any compound such as diacetone peroxide) were observed in the equipment, the acid or the distillate. At steady state, 2.35 gram per minute colourless concentrated acid was pumped out of the three-necked vessel. The concentrated acid had a $H_2SO_4$ content of 58.3% and a $H_2O_2$ content of 1.8%.

In a 2nd concentration step, the concentrated acid of the previous step was dosed to a three-necked glass vessel. The vessel was stirred and the temperature was maintained at about 162° C. by heating with an external oil bath and was connected to a vacuum system at from about 70-120 mbar pressure. The three-necked glass vessel was connected to a condenser and a vessel to collect the condensate. The concentrated acid was dosed at a rate of 2 gram per minute and 0.6 gram per minute condensate was obtained. At steady state, 1.4 gram per minute colourless concentrated acid was pumped out of the three-necked vessel. No solids (any compound such as diacetone peroxide) were observed in the equipment, the acid or the distillate. The concentrated acid had a $H_2SO_4$ content of 83 wt % and a $H_2O_2$ content of <0.5%. The acid was diluted with water to 78 wt % and could be re-used to make 2,5-dimethylhexane-2,5-dihydroperoxide as explained above.

Example 2

To a 2.5 liter reactor—equipped with 3 baffles, a turbine impeller, a thermometer and a cooling mantle—were added 900 gram 70 wt % $H_2SO_4$ and 600 gram 30 wt. % $H_2O_2$. Tert-butyl alcohol (700 gram) was dosed within 1 hour, thereby keeping the temperature in the range from about 35-40° C. The mixture was heated to 45° C. and stirred for 1 hour at this temperature. After that, the mixture was cooled to 30° C. and allowed to separate. The 1.520 g waterlayer had a sulfuric acid concentration of 41 wt %. The organic layer was washed with a bicarbonate solution and contained 668 g of di-tert-butylperoxide with a purity of 99.4% in a yield of 96%.

$H_2O_2$ (102 g, 30 wt %) was added to the waterlayer. The resulting mixture was dosed (rate: 500 ml/hour) to a 100 ml heated vessel that was operated at 93° C. and from about 100-150 mbar, Water vapor was sent to a condenser. The acid flowing out of the vessel was sent to a multicompartment evaporator, in which the temperature was increased to 157° C. at a pressure of from about 100-150 mbar. The colourless acid coming from the last compartment was cooled to room temperature and had a $H_2SO_4$ content of 74 wt %. No solids (any compound such as diacetone peroxide) were observed in the equipment, the acid or the distillate.

After dilution with water to 70 wt % $H_2SO_4$, the acid could be used again in the preparation of ditert-butylperoxide according to the above procedure.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. Process for producing an organic peroxide, said process comprising the following steps:
   a. reacting an alcohol or ketone with hydrogen peroxide, thereby forming a reaction mixture comprising:
   an organic phase comprising an organic peroxide; and
   an aqueous phase comprising (i) at least about 5 wt % H2SO4 and (ii) H2O2 and/or organic peroxide residues,
   b. separating the aqueous phase from the organic phase,
   c. optionally adding H2O2 to, and/or removing any residual organic compounds from, the aqueous phase,
   d. obtaining an additional aqueous phase comprising from about 5-about 60 wt % H2SO4 and about 0.3-about 35 wt % H2O2, and
   e. heating the additional aqueous phase of step d. at a temperature of from about 20-about 300° C., at a pressure of about 0.001 to about 1 bar, thereby decomposing at least part of the H2O2, removing part of the water, and increasing the H2SO4 concentration of the additional aqueous phase by at least about 7 weight percentage points to a concentration of from about 12-about 95 wt %.

2. Process according to claim 1 wherein at least part of the aqueous phase resulting from step e. is re-cycled to step a.

3. Process according to claim 1 wherein the additional aqueous phase of step d. comprises from about 0.5-about 35 wt % H2O2.

4. Process according to claim 1 wherein the additional aqueous phase of step d. comprises from about 10-about 60 wt % H2SO4.

5. Process according claim 1 wherein the H2SO4 concentration of the aqueous mixture resulting from step e. has a concentration of from about 50-about 95 wt % H2SO4.

6. Process according to claim 1 wherein the additional aqueous phase of step d. comprises volatile organic components and step e. further comprises the stripping of the volatile organic components at a temperature of from about 30-about 120° C.

7. Process according to claim 1 wherein step e. further comprises a step of distillation at atmospheric pressure, followed by a step of distillation at a pressure below atmospheric pressure.

8. Process according to claim 1 wherein step e. further comprises a step of distillation wherein the oxygen content in a gas phase of a distillate is kept below the additional aqueous phase of step d. 30 vol % by the addition of nitrogen or air.

9. Process according to claim 1 wherein step e. is conducted in a semicontinuous or a continuous mode.

10. Process according to claim 1 wherein the organic peroxide that is produced is selected from dialkyl peroxides, cyclic ketone peroxides, trioxepanes, and aliphatic hydroperoxides.

11. Process according to claim 10 wherein the organic peroxide that is produced is a dialkyl peroxide selected from the group of 2,2-di(tert-butylperoxy)butane, dicumyl peroxide, di(tert-butylperoxyisopropyl)benzene, 2,5-dimethyl-2,5-di(tert-butylperoxy)hexane, di-tert-butylperoxide, di-tert-amylperoxide, 2,5-dimethyl-2,5-di(tert-butylperoxy)hexyne-3, and tert-butyl cumyl peroxide.

12. Process according to claim 10 wherein the organic peroxide that is produced is an aliphatic hydroperoxide selected from the group of tert-butyl hydroperoxide, tert-amyl hydroperoxide, hexyleneglycol hydroperoxide, 2,5-dimethyl-2,5-dihydroperoxy hexane, 2,5-dimethyl-2,5-dihydroperoxy-3-hexyne, 1,1,3,3-tetramethylbutyl hydroperoxide, and 1,1-dimethylbutyl hydroperoxide.

13. Process according to claim 10 wherein the organic peroxide that is produced is 3,6,9-triethyl-3,6,9-trimethyl-1,4,7-triperoxonane or a mixture of cyclic ketone peroxides comprising 3,6,9-triethyl-3,6,9-trimethyl-1,4,7-triperoxonane.

14. Process according claim 1 wherein an alcohol is reacted with hydrogen peroxide in step a., wherein the alcohol is selected from the group of tert-butyl alcohol, tert-amyl alcohol, and 1,1,3,3-tetramethylbutanol, 2,5-dimethyl-2,5-hexanediol, 2,5-dimethyl-2,5-dihydroxy-hexyne-3, 1,3-bis(isopropanol) benzene, and 1,4-bis(isopropanol) benzene.

15. Process according to claim 1 wherein a ketone is reacted with hydrogen peroxide in step a., wherein the ketone is selected from the group of acetone, acetyl acetone, methyl ethyl ketone, methyl propyl ketone, methyl isopropyl ketone, methyl butyl ketone, methyl isobutyl ketone, methyl amyl ketone, methyl isoamyl ketone, methyl hexyl ketone, methyl heptyl ketone, diethyl ketone, ethyl propyl ketone, ethyl amyl ketone, methyl octyl ketone, methyl nonyl ketone, cyclopentanone, cyclohexanone, 2-methylcyclohexanone, 3,3,5-trimethyl cyclohexanone, and mixtures thereof.

16. Process according to claim 1 wherein the additional aqueous phase of step d. comprises from about 2-about 25 wt % H2O2.

17. Process according to claim 2 wherein the additional aqueous phase of step d. comprises from about 2-about 25 wt % H2O2.

18. Process according to claim 1 wherein the additional aqueous phase of step d. comprises from about 30-about 60 wt % H2SO4.

19. Process according to claim 2 wherein the additional aqueous phase of step d. comprises from about 30-about 60 wt % H2SO4.

* * * * *